United States Patent [19]

Kohn et al.

[11] Patent Number: 5,405,782
[45] Date of Patent: Apr. 11, 1995

[54] DETECTION AND QUANTITATION METHOD FOR THERAPEUTIC AGENTS IN BLOOD

[75] Inventors: Elise C. Kohn, Olney; Lance A. Liotta, Potomac, both of Md.

[73] Assignee: The United States of America as represented by the Secretary of the Department of Health and Human Services, Washington, D.C.

[21] Appl. No.: 41,438

[22] Filed: Mar. 31, 1993

[51] Int. Cl.[6] ............................................. G01N 30/02
[52] U.S. Cl. .................................... 436/161; 73/61.52; 210/656; 436/63; 436/175; 436/178
[58] Field of Search ............... 436/63, 161, 175, 177, 436/178; 422/70; 73/61.52, 61.53, 61.55; 210/656

[56] References Cited

U.S. PATENT DOCUMENTS

| | | | |
|---|---|---|---|
| 4,590,201 | 5/1986 | Bochis et al. | 514/359 |
| 5,011,608 | 4/1991 | Damjanovic | 210/656 |
| 5,132,315 | 7/1992 | Kohn et al. | 514/359 |

OTHER PUBLICATIONS

Holmes et al., Journal of Chromatography, Biomedical Applications, vol. 613, Apr. 6, 1993, pp. 317–325.
Nomura et al., Journal of Chromatography, Biomedical Applications, vol. 572, Dec. 6, 1991, pp. 333–338.
Dunnett et al., Journal of Chromatography, Biomedical Applications, vol. 579, 1992, pp. 45-53.
Kohn et al., Cancer Research, vol. 52, Jun. 1, 1992, pp. 3208–3212.
Arnaud et al., Journal of Chromatography, Biomedical Applications, vol. 572, Dec. 6, 1991, pp. 103–116.
Klima et al., Journal of Chromatograpy, Biomedical Applications, vol. 385, 1987, pp. 357–361.
Felder et al., Journal of Pharmacology and Experimental Therapeutics, vol. 257, No. 3, Jun. 1991, pp. 967–971.
Hupe et al., Journal of Biological Chemistry, vol. 266, No. 16 Jun. 5, 1991, pp. 10136–10142.
Brunner, L. A., et al., "An Automated Method for the Determination of a New Potential Antiepileptic Agent (CGP 33101) in Human Plasma Using High Performance Liquid Chromatography," *Biomedical Chromatography*, 6:278–282 (1992).
J. Alvarez–Builla, et al., "High–Performance Liquid Chromatographic Determination of the $\pi$ Values of Azol–N–yl Substituents," *J. of Pharmaceutical Sciences*, 81(6):577-580 (Jun. 1992).
Database WPI, Section Ch, Week 9210, Derwent Publications Ltd., London, GB; Class B04, AN 92-148003 and JP 4091096 (Suntory Ltd) 24 Mar. 1992 (Abstract).
Stephen M. Longnecker, et al, "High–Performance Liquid Chromatographic Assay for Taxol in Human Plasma and Urine and *Pharmacokinetics* in a Phase 1 Trial", in: Cancer Treatment Reports vol. 71, No. 1, Jan. 1987, pp. 53–59.
Roman M. Chicz, et al, "High Performance Liquid Chromatography: Effective Protein Purification by Various Chromatographic Modes", in: Methods in Enzymology, vol. 182, pp. 392–421.
Raymond G. Morris, "Improved High-Performance Liquid Chromatography Assay for Atenolol in Plasma and Urine Using Fluorescence Detection", in: Therapeutic Drug Monitoring, vol. 13, No. 4, 1991, pp. 345–349.

(List continued on next page.)

*Primary Examiner*—James C. Housel
*Assistant Examiner*—Maureen Wallenhorst
*Attorney, Agent, or Firm*—Townsend and Townsend Khourie and Crew

[57] ABSTRACT

The present invention relates to an improved method for the determination of therapeutic agents in blood. This method utilizes a solid phase extraction of the solute from plasma followed by reverse phase high performance liquid chromatography on a column of irregularly shaped C-18 modified silica. Comparison of the produced chromatogram with a standard curve provides a precise and accurate quantification of the amount of the solute in blood. Additionally, the extraction and chromatography steps can be readily automated for the rapid determination of multiple samples.

15 Claims, 3 Drawing Sheets

OTHER PUBLICATIONS

J. M. Streete, et al, "The Analysis of Clobazam and its Metabolite Desmethylclobazam by High-Perfomance Liquid Chromatography", in: Therapeutic Drug Monitoring, vol. 13, No. 4 (1991), pp. 339–344.

C. S. Stockley, et al, "Stereo High-Performance Liquid Chromatographic Assay for the Enantiomers of Phenylpropanolamine in Human Plasma", in: Therapeutic Drug Monitoring, vol. 13, No. 4 (1991) pp. 332–338.

Diuseppe Carlucci, et al, "Determination of Rufloxacin, a New Tricyclic Fluoroquinolone in Biological Fluids Using High-Performance Liquid Chromatography with Ultraviolet Detection", in: Therapeutic Drug Monitoring, vol. 13, No. 5 (1991), pp. 448–451.

A. G. Johnson, et al, "Improved High-Performance Liquid Chromatographic Method for the Determination of Indomethacin in Plasma", in: Therapeutic Drug Monitoring, vol. 14, No. 1 (1992), pp. 61–64.

Asko Riutta, et al, "Solid-Phase Extraction of Urinary 11-Dehydrothromboxane $B_2$ for Reliable Determination with Radioimmunoassay", in: Analytical Biochemistry 202 (1992), pp. 299–305.

DETECTION AND QUANTITATION METHOD FOR THERAPEUTIC AGENTS IN BLOOD

FIELD OF THE INVENTION

This invention relates to a method for determining the concentration of therapeutic agents in a blood sample.

BACKGROUND OF THE INVENTION

The development of new and more effective therapeutic agents often requires clinical studies in which the amount of the agent circulating in blood can be monitored. In particular, many anti-cancer agents must maintain a threshold concentration in blood to effectively block the growth and metastasis of their target cancers.

A variety of methods exist for monitoring the levels of drugs in blood. Most common is a method involving high performance liquid chromatography (HPLC). To utilize HPLC, the solute of interest must first be separated from the majority of blood components. This is typically done using a liquid phase extraction process which is often tedious, time consuming, and messy. The multistep liquid phase extraction often involves partitioning the sample between two solvents (usually an aqueous/organic mixture), drawing off and discarding the aqueous solvent, filtering the organic solvent to remove any particulate matter, evaporating the organic solvent and finally reconstituting the residue in a solvent suitable for the subsequent chromatographic separation. The conditions to be used for chromatography involve consideration of numerous parameters. Most important are the stationary phase or column packing and the elution mobile phase.

The materials most commonly used for packings in HPLC columns are microparticulate silicas. These small porous silica particles have either a spherical or irregular shape and a nominal diameter of 3, 5 or 10 μm. Additionally, the silica is often chemically modified or "bonded" with a variety of organic residues to alter the size, shape and pore size of the silica particle, the carbon content of the bonded phase and the extent of end-capping. End-capping is a method used to reduce the residual adsorptive properties of the silica. The result of these modifications is a wide variety of column packings from many manufacturers including a trend toward "application-specific" column packings.

The composition of the mobile phase controls a separation more than any other factor. Most separations utilize a binary solvent mixture as mobile phase, however ternary or quaternary compositions also work. If the composition of the mobile phase is constant, the elution is called "isocratic". Alternatively, the composition of the mobile phase can be made to change in a predetermined manner during the separation by using programmed solvent mixing systems. Elution done in this manner is known as "gradient" elution. Gradient elution is used in situations when the range of column retention times for a series of solutes is so large that they cannot be eluted in a reasonable time using a single solvent or solvent mixture. For example, if a sample contains compounds having a wide range of polarities, the separation can be carried out by changing the polarity of the solvent mixture during separation.

The terms normal phase and reverse phase chromatography are used to describe a number of separations. In normal phase chromatography the polarity of the stationary phase is higher than that of the mobile phase. These parameters are achieved when non-bonded silica is used in adsorption chromatography. Reverse phase means that the polarity of the stationary phase is lower than that of the mobile phase. This result is achieved when the silica is hydrocarbon-bonded and the mobile phase is polar. For either type of chromatography the solutes elute in order of their polarity, the most polar elute first with reverse phase and the least polar elute first with normal phase.

Reverse phase HPLC offers the further advantage that numerous bonded stationary phases are available to increase the scope of separations which can be obtained. Furthermore, the mobile phase is often an aqueous mixture which reduces solvent costs. Methods have been described for the reverse phase HPLC determination of taxol (Longnecker, et al., Cancer Treat. Rep., 71:53–59 (1987)), clobazam (Streete, et al., Ther. Drug Monit., 13:339-344 (1991)), indomethacin (Johnson, et al., Ther. Drug Monit., 14:61-65 (1992)), rufloxacin (Carlucci, et al., Ther. Drug Monit., 13:448-451 (1991)) and phenylpropanolamine (Stockley, et al., Ther. Drug Monit., 13:332-338 (1991)).

A new anti-cancer agent 1, (CAI) 5-amino-1-(4-(4-chlorobenzoyl)-3,5-dichlorobenzyl)-1,2,3-triazole-4-carboamide, has recently been discovered and is now in clinical trial. This compound has been shown to inhibit signal transduction pathways and cancer growth in human xenograft models in the concentration range 1-10 μg/mL. Quantitation of 1 in blood has been conducted by precipitating plasma samples with trichloroacetic acid, extracting the samples with methylene chloride, reconstituting the concentrated extract and chromatographing the resultant extract using HPLC. This method provides good sensitivity but requires lengthy liquid extraction steps and is not amenable to automation. To support the clinical trials and subsequent use of this and related compounds, a quantitation method is required which is reliable, straightforward, accurate and amenable to automation.

SUMMARY OF THE INVENTION

It has now been discovered that an unusually efficient and precise determination of the levels of compound 1 and related analogs in blood can be achieved using a modification of the liquid extraction/HPLC technique. According to this modification, a solid phase organic extraction of the solute from plasma is conducted by passing the plasma through a C-18 cartridge which is attached to a vacuum manifold. The vacuum provides a more rapid extraction and use of a manifold allows simultaneous extraction of multiple samples. The cartridges are eluted with a polar organic solvent, the solvent is evaporated, and the sample is reconstituted in a buffer prior to HPLC analysis. Chromatography is conducted using isocratic elution on a reverse phase column having irregular column packing. These steps are easily automated and result in surprisingly quick, accurate and reproducible determinations of circulating plasma concentrations of compound 1 and its analogs.

DESCRIPTION OF THE PREFERRED EMBODIMENT

As used herein, the term "alkyl" refers to a saturated hydrocarbon radical which may be straight-chain or branched-chain (for example, ethyl, isopropyl, t-amyl, or 2,5-dimethylhexyl). Preferred alkyl groups are those containing 1 to 6 carbon atoms. All numerical ranges in this specification and claims are intended to be inclusive of their upper and lower limits.

The term "alkoxy" refers to an alkyl radical as described above which also bears an oxygen substituent which is capable of covalent attachment to another hydrocarbon radical (such as, for example, methoxy, ethoxy, phenoxy and t-butoxy).

The term "aromatic group" refers to a moiety which has multiple sites of unsaturation, and may be a single ring or multiple rings which are fused together or linked covalently. The aromatic rings may each contain heteroatoms, for example, phenyl, naphthyl, biphenyl, thienyl, pyridyl and quinoxalyl. The aromatic moieties may also be optionally substituted with halogen atoms, or other groups such as nitro, carboxyl, alkoxy, alkyl, amino, amido, carboxylic esters, alkylthio, cyano and the like.

The term "alkoxyalkyl" refers to an alkoxy radical attached directly to an alkyl group.

The term "hydrophobic radical" refers to a group which lowers the water solubility of a molecule. Preferred hydrophobic radicals are groups containing at least 3 carbon atoms.

The term "substituted" refers to groups having additional moieties attached, such moieties including halogen atoms, and groups such as nitro, carboxyl, alkoxy, alkyl, amino, amido, carboxylic esters, alkylthio, cyano and the like.

The present invention broadly consists of an improved method for detecting and quantifying an amount of a therapeutic agent in blood. In this method the therapeutic agents are compounds of the formula;

In formula A, p is an integer of from 0 to 4, $Ar^1$ is —$Ar^2$—X—$Ar^3$, phenyl, trioxaadamantyl, anthracenyl, anthraquinonyl, naphthyl, phenanthryl, or their substituted versions, $Ar^2$ and $Ar^3$ are each aromatic moieties and are independently phenyl, naphthyl, or their substituted versions, X is a linking moiety such as O, S, $SO_2$, CO, CHCN, straight chain alkyl, alkoxy, and alkoxyalkyl, and Z is a nitrogen-containing heterocyclic moiety such as imidazolyl, 1,2,3-triazolyl, 1,2,4-triazolyl, pyrazinyl, purinyl, pyrimidinyl, 1,2,3-triazolo-{4,5-d}-pyrimidinyl, and their substituted versions.

The steps of this improved method involve,
(a) extracting the therapeutic agents from a blood sample using a solid phase procedure to produce an extract;
(b) chromatographing the extract using an isocratic elution with a reverse phase high performance liquid chromatography column having irregular packing, to produce a chromatogram; and
(c) comparing the chromatogram produced in step (b) with a standard.

These steps are particularly suited for automation, thereby enhancing the utility of the method. The solid phase procedures may be carried out using a vacuum manifold which permits from 12 to 24 samples to be extracted simultaneously. Additionally, special tubes packed with appropriate solid-phase extraction matrices which are compatible with laboratory robots are now commercially available. Further automation can be achieved using any of the commercially available auto samplers designed for use with the HPLC instrument employed.

In the present inventive method a blood sample is centrifuged and the plasma is drawn off, filtered and extracted using solid phase techniques. The solid phase techniques involve applying the plasma to a cartridge packed with a solid phase matrix such as a chromatography support. The cartridge is washed with a buffer then eluted with a polar solvent. The sample eluate containing the therapeutic agent to be determined is concentrated and chromatographed using isocratic reverse phase HPLC. Isocratic reverse phase HPLC is carried out by first suspending the concentrated sample in a small volume of the mobile phase, injecting the sample onto a column having an irregular column packing and eluting the column with an isocratic solvent mixture. The column eluate is monitored with a UV detector and the results are displayed on a chromatogram. Comparison of a sample chromatogram with a standard series provides a quantification of the amount of therapeutic agent in blood.

The solid phase extraction is preferably carried out using a cartridge packed with hydrocarbon-bonded silica. More preferably, the cartridge is packed with C-18 bonded silica. The cartridge packing is typically conditioned prior to use by treating the packed cartridge with methanol followed by treatment with an aqueous buffer. Once conditioned, the cartridge is loaded with the plasma sample, rinsed with an aqueous buffer and eluted with an organic solvent, preferably methanol. Removal of solvent from the eluate by evaporation produces an extract containing the therapeutic agent to be determined. Evaporation of the organic solvent may be carried out under reduced pressure, at elevated temperature or by passing a continuous stream of nitrogen, argon or air over the solution. The resultant extract can be chromatographed without further manipulation.

The present inventive method utilizes isocratic reverse phase high performance liquid chromatography to separate the therapeutic agent from the standard as well as any interfering components. The stationary phase used in this method is a silica packing having an irregular shape. While spherical silica particles provide advantages over irregular particles such as efficiency and permeability the irregular materials exhibit selectivity different from most spherical materials. This selectivity is generally due to differences in surface area and the carbon load achieved by derivatization of the silanol groups on the silica particles. In the present inventive method the stationary phase is derivatized to produce a non-polar surface. Such derivatized stationary phases are suitable for separating relatively non-polar compounds from a polar solvent matrix. A preferred column packing to be used for the stationary phase is hydrocarbon-bonded silica having a size of from about 2 to 25 microns. More preferably, the irregular packing is either C-8, C-18 or cyclohexyl bonded silica. Most preferred is a column packing of irregular C-18 hydrocarbon-bonded silica having a size of about 10 microns. The composition of the mobile phase used in the present method is held constant and is typically a mixture of a polar organic solvent and a buffered aqueous solution. A preferred mobile phase consists of a mixture of methanol and aqueous ammonium acetate. More preferably the mobile phase consists of methanol and about 0.05–0.5M aqueous ammonium acetate. Still further preferred is a mobile phase consisting of about 60–90% methanol and about 10–40% 0.1M aqueous ammonium acetate.

A number of other factors may be varied within the invention without detracting from the improved nature of the method. These factors include the manner in which centrifugation of the blood sample is conducted, the amount and nature of the internal reference which is added to the sample, the volume of solvent used to extract the sample-laden solid phase extraction cartridge, the pumping rate at which reverse phase HPLC is conducted and the methods of detection used for the HPLC column eluate.

A blood sample is centrifuged for a sufficient period of time and at a sufficient speed such that the plasma becomes separated from suspended, particulate matter. Typically centrifugation will require times of at least eight minutes at speeds of greater than about 2500 rpm for a one-mL sample. Preferably, centrifugation will be carried out for about twelve minutes at speeds of about 3000 rpm. The plasma is drawn off and an internal standard is added to the plasma. The standard should be a compound which is inert to the conditions of both the solid phase extraction and subsequent reverse phase HPLC methodology. Additionally, the standard should be easily separated from the therapeutic agent of interest and should be readily detectable using the same detection method chosen for the therapeutic agent. A preferred internal standard is harmine (compound 2, available from Sigma Chemical Co., St. Louis, Mo., USA), which is hydrophobic, stable to the extraction and chromatography conditions and is readily separated from compound 1. Furthermore, the amount of internal standard used should produce a readily detectable peak on the resultant chromatogram without "swamping out" the other signals. In the present method, an amount of about 1 μg of harmine per mL of sample is preferred.

2

The amount of solvent used to remove the therapeutic agent of interest from the solid phase extraction matrix is not critical. However, the use of an insufficient amount may result in incomplete removal of the therapeutic agent and use of an excess amount will require longer times to remove the solvent prior to chromatography. When a plasma sample of about 1 mL is applied to a solid phase extraction cartridge, elution with about 4 mL of methanol is preferred. After the solvent is removed, the sample is taken up in a small portion of the mobile phase to be used in the subsequent chromatography and is injected onto the column.

The rate at which the mobile phase is passed through the column is also not critical. When an analytical column (250 mm × 4.5 mm) having a preferred adsorbent is used, a flow rate of about 1.0 mL/min produces an optimal separation the therapeutic agent of interest from harmine. This preferred separation requires less than twenty minutes.

Finally, the method of detection is not critical and any of the conventional means such as UV detection or refractive index detection may be used. The preferred method of detection is UV detection.

In addition to the preferred aspects for the particular steps of the invention, there are certain preferred embodiments for the therapeutic agents which may be detected using this method.

In certain preferred embodiments, this method is for the detection and quantification in blood of a therapeutic agent of formula A in which p is an integer of from 0 to 2, $Ar^1$ is —$Ar^2$—X—$Ar^3$, $Ar^2$ and $Ar^3$ are both substituted phenyl, and Z is substituted or unsubstituted imidazolyl or 1,2,3-triazolyl.

In another preferred embodiment, this method is for the detection and quantification in blood of a therapeutic agent of formula A in which $Ar^1$ is —$Ar^2$—X—$Ar^3$, $A^2$ and $Ar^3$ are both substituted phenyl, X is O, CO, and CHCN, Z is substituted or unsubstituted imidazolyl or 1,2,3-triazolyl, and p is 1.

In further preferred embodiments, this method is for the detection and quantification in blood of a therapeutic agent of formula A in which $Ar^1$ is —$Ar^2$—X—$Ar^3$, $Ar^2$ and $Ar^3$ are both substituted phenyl, Z is substituted or unsubstituted imidazolyl or 1,2,3-triazolyl, X is CO, and p is 1.

In still further preferred embodiments, this method is for the detection and quantification in blood of a therapeutic agent of formula A in which $Ar^1$ is —$Ar^2$—X—$Ar^3$, $Ar^2$ and $Ar^3$ are both substituted phenyl, X is CO, Z is 5-amino-4-carboxamido-1,2,3-triazolyl, and p is 1.

In even further preferred embodiments, this method is for the detection and quantification in blood of a therapeutic agent of formula A in which $Ar^1$ is —$Ar^2$—X—$Ar^3$, $Ar^2$ is 2,6-dichlorophenyl, $Ar^3$ is 4-chlorophenyl, X is CO, Z is 5-amino-4-carboxamido-1,2,3-triazolyl, and p is 1.

In a most preferred embodiment, the method is useful for the detection and quantification in blood of a therapeutic agent of formula A in which $Ar^1$ is $-Ar^2-X-Ar^3$, $Ar^2$ is 2,6-dichlorophenyl, $Ar^3$ is 4-chlorophenyl, X is CO, Z is 5-amino-4-carboxamido-1,2,3-triazolyl, and p is 1 and involves (a) extracting the therapeutic agent from blood using solid phase extraction on a chromatography cartridge packed with a C-18 hydrocarbon-bonded silica,
 (b) chromatographing the product of step (a) on a column having 10 micron C-18 hydrocarbon-bonded irregular column packing using an isocratic elution with a mobile phase consisting of 60–90% methanol and 10–40% 0.1M aqueous ammonium acetate, to produce a chromatogram, and
 (c) comparing the chromatogram of step (b) with a standard.

The following experimental results are offered by way of example and not by way of limitation.

EXAMPLE 1

This example demonstrates the general procedures for the determination of compound 1 in blood plasma using solid phase extraction and isocratic reverse phase HPLC.

Reference samples of compound 1 in plasma (weight/weight) were made fresh daily and kept at 4° C. until use. Additionally, harmine was added to each sample as an internal reference to final concentration of 1 μg/mL. Harmine was used as the internal standard because of its hydrophobic nature, stability under these reaction conditions and ease of separation from compound 1. Detection of compound 1 in plasma was not altered by up to two freeze and thaw cycles of the reference samples.

Extraction of compound 1 from plasma samples was accomplished with a solid phase matrix attached to a vacuum manifold. One mL aliquots of samples were separately centrifuged at 3000 rpm for 12 minutes at 4° C., and then filtered. The filtrate was then applied to a 300 mg C-18 Maxi-Clean ™ cartridge (from Alltech Association, Inc., Deerfield, Ill., USA) that had been pretreated with 10 mL of methanol followed by 10 mL of 0.1M ammonium acetate buffer (pH 6.5). The sample-laden cartridges were rinsed with the ammonium acetate buffer (12 mL) and then eluted with 4 mL of methanol. Solvent was evaporated from the eluate under a continuous stream of nitrogen and the residue was suspended in 500 μL of a buffer consisting of methanol and 0.1M ammonium acetate, pH 6.5 (73/27, volume/volume). The resulting sample was filtered through an acrodisc 0.2 μm filter (Gelman Sciences, Ann Arbor, Mich., USA).

Figure 1:
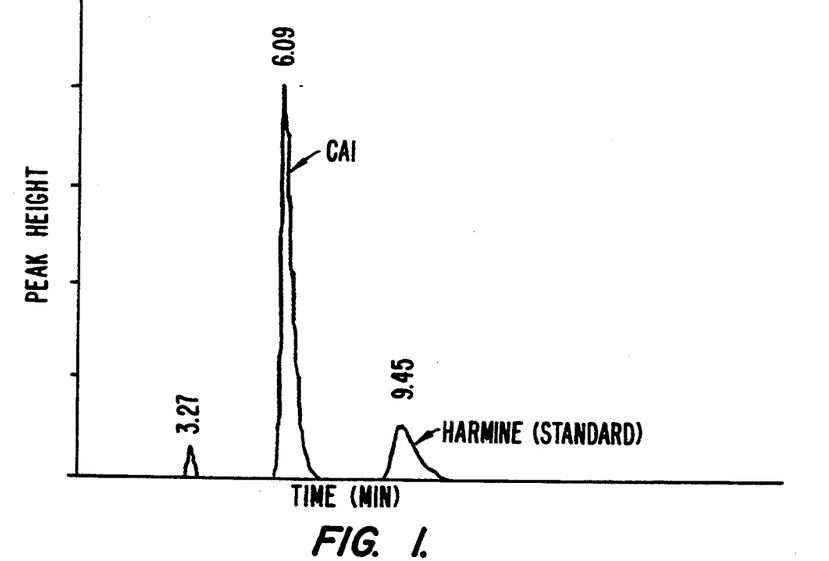
FIG. 1 shows a sample chromatograph of compound 1 (at 6.09 minutes) with barmine (at 9.45 minutes) as an internal standard.

Chromatographic separation of compound 1 from the remaining components was carried out using a computerized Gilson dual pump HPLC system with an autosampler. Fifty microliter aliquots of the samples were drawn up by the autosampler and subjected to reverse phase chromatography over a C-18 analytical column having irregular 10 μm adsorbant (250 mm×4.6 mm, Thomson Scientifics, Springfield, Va., USA) preceded by a spherical C-18 guard cartridge and a 100 μL injection loop. The guard column was changed approximately monthly to maintain solvent pressure and to prolong the life of the analytical column. The analytical column was reversed and washed with methanol, water, and 50% methanol/49% HPLC grade water/1% acetic acid approximately every 150 runs and changed after 1200 runs. Optimal chromatographic separation of compound 1 and harmine was accomplished over 18 minutes using an isocratic elution of 73% methanol and 27% 0.1M ammonium acetate buffer (pH 6.5) at a flow rate of 1.0 mL/min. The mobile phase was prepared, filtered and degasseal daily. FIG. 1 shows an HPLC chromatogram obtained using this method. The peak at 6.09 minutes corresponds to compound 1, while the peak at 9.45 minutes is the internal reference harmine (compound 2).

The amount of compound 1 in a sample was determined by comparing the peak area in the sample chromatogram to a calibration curve corresponding to a concentration range which bracketed the therapeutic window required for activity. The standards used for the calibration curve were prepared in duplicate in fresh plasma and were extracted according to the procedure above. Standard curves were repeated weekly and fresh standard samples were included with each chromatography series. These standard samples consisted of duplicate aliquots of 0.5 and 2.0 μg/mL of compound 1 in plasma. Calibration curves were constructed by plotting the concentration of compound 1 versus the area of the compound 1 peak.

EXAMPLE 2

This example illustrates the efficiency of the extraction procedure for analyzing the recovery of compound 1 from plasma.

Figure 2:
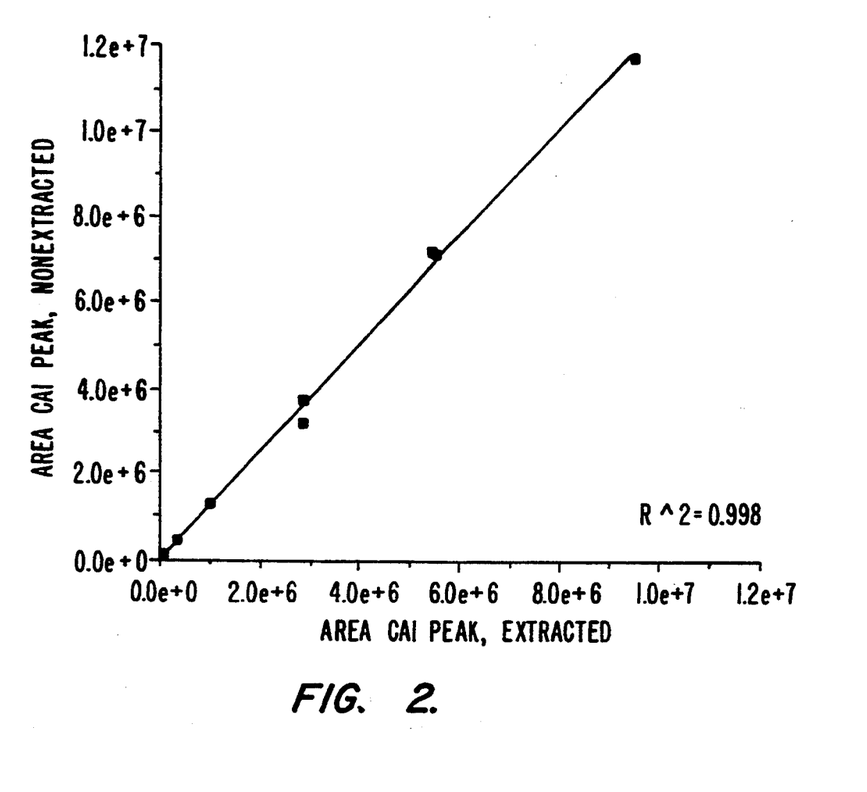
FIG. 2 illustrates the efficiency of recovery for compound 1, comparing the chromatogram peak areas for nonextracted and extracted samples.

The efficiency of the extraction procedure was determined by analyzing the recovery of compound 1 from extracted plasma samples containing gravimetric amounts of compound 1. The samples (containing harmine as an internal standard) were extracted and chromatographed using the procedure of Example 1. The area of the HPLC peak corresponding to compound 1 was measured for each of the gravimetric samples. FIG. 2 shows a comparison of the HPLC peak area for compound 1 from these extracted plasma samples with the HPLC peak areas for standards made up of various amounts of compound 1 diluted directly in the mobile phase. The recovery of compound 1 from plasma samples was consistent (~80%) over the full concentration range as shown in the Figure ($r^2 = 0.998$). Additionally, consistent recovery of harmine was observed within and between runs (coefficient of variability $\leq 6\%$).

EXAMPLE 3

This example illustrates the precision and accuracy of the present inventive method.

The precision and accuracy of the inventive method were determined by repetitive sampling of plasma containing known concentrations of compound 1. Fifteen replicate gravimetric samples of fresh plasma containing 2.0 μg/mL compound 1 were extracted and then chromatographed daily for five days.

Accuracy

Figure 3:
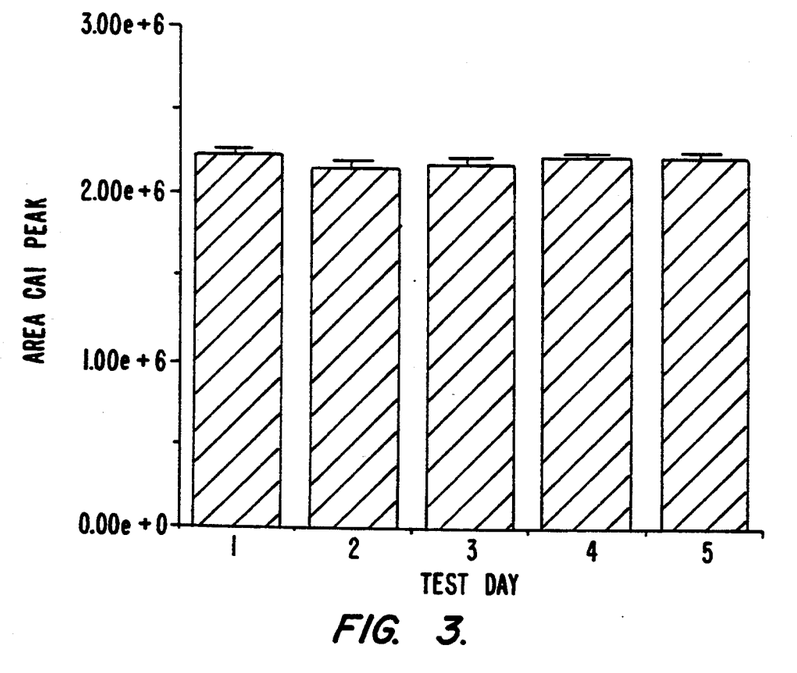
FIG. 3 illustrates the precision and accuracy of compound 1 quantitation by showing the mean and standard deviation of 15 replicates over 5 days.

The coefficient of variability within the fifteen-sample batch provides an indication of accuracy for the inventive method. Thus, aliquots from the fifteen samples were extracted daily over a five day period and chromatographed using the method described in Example 1. The area of the compound 1 peak was measured and the mean for the fifteen samples was calculated on each day. The standard deviation from the mean was also determined for the sample series. Finally, the coefficient of variability (%) was calculated as the (standard deviation/area mean)×100. The results are shown in Table IA and FIG. 3. The coefficient of variability ranged from 3.7% to 6.8%, indicating an excellent degree of accuracy.

Precision

The coefficient of variability within a particular sample over the five day test period provides an indication of precision. An aliquot from each sample was removed daily and extracted and chromatographed as described in Example 1. The area of the peak corresponding to compound 1 was measured from each chromatogram. After five days the area mean was calculated for the five chromatograms from each sample. The standard deviation from the mean was also determined for the sample series and the coefficient of variability was calculated as above. The results are shown in Table IB. The coefficient of variability for the fifteen samples over five days ranged from 0.3% to 7.5% and indicate an excellent degree of precision.

The reliability of this assay was further confirmed for a range of concentrations. A series of five samples each of 0.05 µg/mL, 0.5 µg/mL and 5.0 µg/mL compound 1 (gravimetric) in plasma were extracted and chromatographed as above. The peak areas were measured for each sample and the coefficient of variability for each concentration was determined as follows: 9.7% for 0.05 µg/mL, 4.7% for 0.5 µg/mL, and 5.7% for 5.0 µg/mL.

TABLE I

Accuracy and Precision of Chromatography of Repetitive Samples of Known Compound 1 Concentrations in Human Plasma

| Day Sample | Area (mean ± S.D.) | Coefficient of Variability (%) |
|---|---|---|
| A Within Run n = 15 samples | | |
| 1 | 2232090 ± 128650 | 5.3 |
| 2 | 2154886 ± 128650 | 6.0 |
| 3 | 2177826 ± 137749 | 6.3 |
| 4 | 2230454 ± 81978 | 3.7 |
| 5 | 2226915 ± 152479 | 6.8 |
| B Between Run n = 5 days | | |
| 1 | 2338591 ± 43700 | 1.8 |
| 2 | 2114022 ± 159000 | 7.5 |
| 3 | 2224707 ± 105000 | 4.7 |
| 4 | 2188818 ± 101000 | 4.6 |
| 5 | 2173757 ± 85400 | 3.9 |
| 6 | 2309301 ± 39000 | 1.7 |
| 7 | 2065886 ± 83300 | 4.0 |
| 8 | 2227422 ± 94900 | 4.3 |
| 9 | 2190967 ± 95100 | 4.3 |
| 10 | 2176976 ± 123000 | 5.6 |
| 11 | 2022007 ± 70100 | 3.5 |
| 12 | 2218563 ± 108000 | 4.9 |
| 13 | 2233748 ± 94800 | 4.2 |
| 14 | 2209108 ± 96700 | 4.4 |
| 15 | 2411476 ± 8290 | 0.3 |

EXAMPLE 4

This example illustrates the linearity of results achieved using the solid-phase extraction and chromatographic procedure of the present inventive method over a greater than one thousand-fold concentration range.

Figure 4:
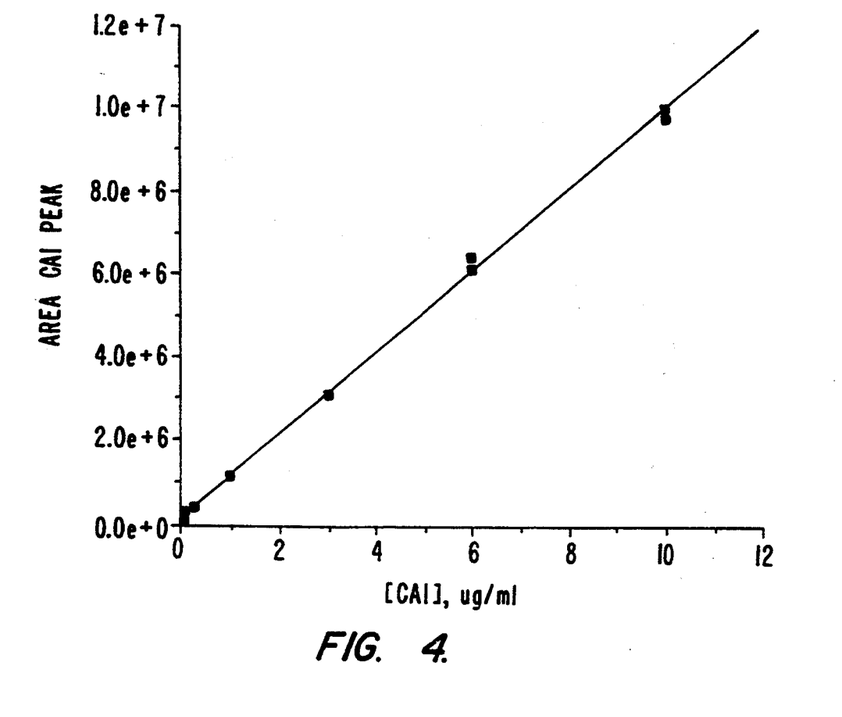
FIG. 4 shows a standard curve of gravimetric concentrations of compound 1.
Figure 5:
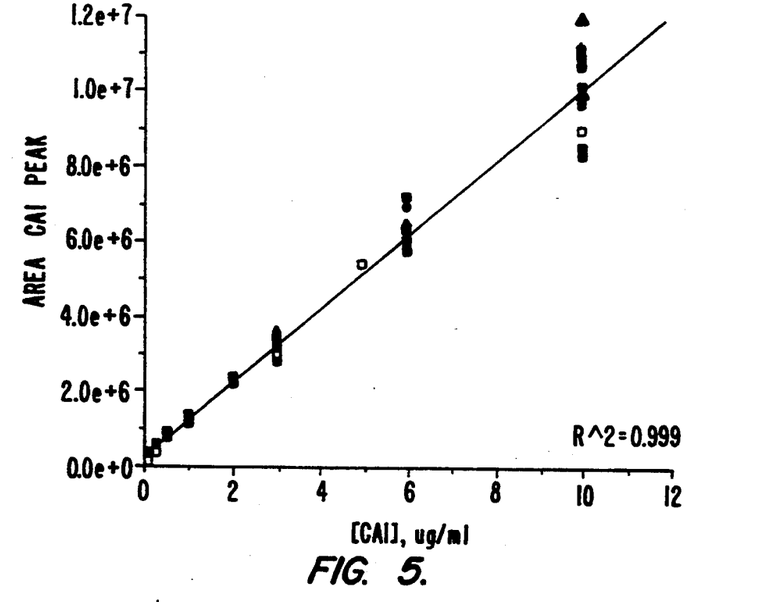
FIG. 5 shows a composite standard curve of gravimetric concentrations of compound 1.

The concentration range selected for this determination was based on in vitro and animal data. The range was from 0.04 µg/mL up to 10 µg/mL compound 1. FIG. 4 shows a plot of the compound 1 peak area (y-axis) versus the concentration of compound 1 (x-axis). Additionally, a series of standard curves for compound 1 extracted from plasma was linear over the concentration range 0.04–10.0 µg compound 1 per milliliter of plasma ($r^2 = 0.999$, n=8). FIG. 5 shows the data points for this series with the line representing the composite.

The slope and y-intercept of this series of standard curves are shown in Table II. The lower end of reliable detection was 0.04 µg/mL and the upper limit has not been determined.

TABLE II

Linearity of Compound 1 Standard Curves Over the Concentration Range 0.04–10.0 µg/mL

| Curve | y-Intercept[a] ($\times 10^5$) | m ($\times 10^4$) | $r^{2b}$ |
|---|---|---|---|
| 1 | 3.8163 | 9.222 | 0.994 |
| 2 | 3.7477 | 8.404 | 0.993 |
| 3 | 2.1997 | 10.987 | 0.997 |
| 4 | 2.3732 | 10.418 | 0.998 |
| 5 | 1.2274 | 10.986 | 0.998 |
| 6 | 1.6565 | 9.893 | 0.999 |
| Composite (n = 8) | 1.6565 | 9.893 | 0.999 |

[a]Equation from linear regression: y = mx + b.
[b]Linear regression statistic calculated using CricketGraph (Malvern, Pennsylvania, USA)

EXAMPLE 5

This example illustrates the application of the present method to the determination of compound 1 in the plasma of patients receiving orally administered compound 1.

Patients were treated daily with orally administered compound 1 (100 mg/m² per day) on a clinical Phase I study. Compound 1 was dissolved in PEG-400 at 100 mg/mL and was taken after an 8-hour fast. Patient plasma samples were obtained from either heparinized blood or blood with EDTA added as a coagulant. The samples were centrifuged at 2500 g for 10 min. Gravimetric compound 1 plasma reference samples were made fresh each day. Samples were kept at 4° C. until use, however, up to two freeze-thaw cycles of compound 1-containing plasma did not alter compound 1 detection.

Extraction of the samples and chromatography was carried out as described in Example 1. Quantitation of compound 1 concentrations in patient samples and assay performance samples were calculated using the equation derived from the single variable linear regression of the plotted calibration curves, y=mx+b, where y is the peak area of the 6.1-min peak, and m and b were calculated by linear regression analysis. Blood samples taken prior to drug administration constituted negative controls and were always devoid of compound 1 on chromatographic analysis. Repetitive analysis of the patient samples further validated the chromatographic assay. Table III shows the results of 0-, 4- and 24-hour and 28-day blood samples for the first four patients on the clinical trial of daily oral administration of compound 1. The 28-day duplicate plasma samples were assayed five times each.

Figure 6A:
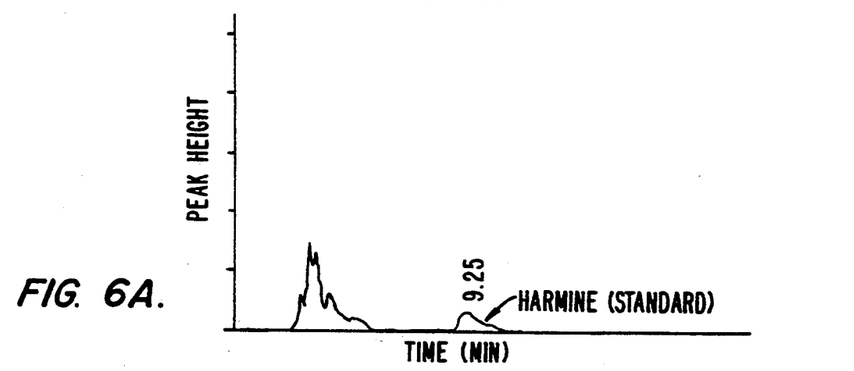
FIG. 6A and 6B show chromatograms from patient samples pre- and post-treatment with compound 1, respectively.
Figure 6B:
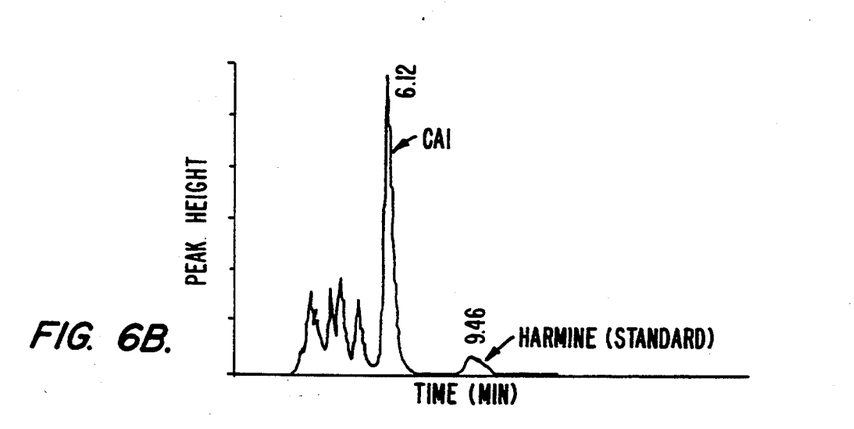

FIG. 6 illustrates two chromatograms from patient #2. In FIG. 6A, the blood sample was taken prior to initiation of compound 1 therapy and there is an absence of any peak corresponding to compound 1. However, harmine eluted at 9.25 min. FIG. 6B shows the chromatogram from a blood sample taken at the completion of 28 days of daily oral compound 1 administration. Compound 1 eluted at 6.12 min and harmine eluted at 9.46 min.

TABLE III

Quantitation of Unknown Compound 1 Levels In Individual Patient Samples

| Pa- | Compound 1 level (μg/mL) | | | | Compound 1 levels (mean ± S.D.) | Coefficient of Variability |
|---|---|---|---|---|---|---|
| tient | 0 h | 4 h | 24 h | 28 d | μg/mL | (%) |
| 1 | 0 | 0.434 | 0.274 | 1.075 | 0.981 ± 0.056 | 5.6 |
| 2 | 0 | 0.923 | 1.152 | 3.610 | 3.974 ± 0.204 | 5.1 |
| 3 | 0 | 0.433 | 0.233 | 3.528 | 3.629 ± 0.057 | 1.56 |
| 4 | 0 | 0.421 | 0.073 | 3.078 | 3.125 ± 0.028 | 0.89 |

EXAMPLE 6

This example shows the reverse phase HPLC retention times for a series of compounds related to compound 1 using the present inventive method. The retention times are shown in Tables IV and V and are for samples run without any added harmine as standard. As the retention times indicate, all compounds would be readily separable from harmine using the present inventive method.

TABLE IV

Reverse Phase HPLC Retention Times for Analogs of Compound 1

| Compound Number | A | B | C | Retention Time (min) |
|---|---|---|---|---|
| 1 | N | carboxamido | amino | 6.1 |
| 3 | N | carboxamido | formamido | 6.2 |
| 4 | N | carboxamido | acetamido | 6.2 |
| 5 | N | carboxamido | benzamido | 6.2 |
| 6 | N | carboxyl | amino | 6.2 |
| 7* | N | carboxamido | amino | 4.86 |

*all Cl are replaced by H

TABLE V

Reverse Phase HPLC Retention Times for Analogs of Compound 1

| Compound Number | D | E | Retention Time (min) |
|---|---|---|---|
| 8 | F | H | 3.5 |
| 9 | Cl | H | 3.55 |
| 10 | Br | H | 3.65 |
| 11 | I | H | 4.16 |
| 12 | F | F | 4.42 |

Compound 1 can be prepared by the method described in U.S. Pat. No. 4,590,201.

Compounds 3–5 are prepared by treating compound 1 with the appropriate anhydride (formic acetic anhydride, acetic anhydride, or benzoic anhydride).

Compound 6 can be prepared by treating compound 1 with sufficient acid to hydrolyze the carboxamide to a carboxylic acid.

Compound 7 can be synthesized beginning with 4-methylbenzophenone. Treatment of 4-methylbenzophenone with N-bromosuccinimide provides 4-bromomethylbenzophenone which is converted to its corresponding azide using sodium azide in ethanol. Treatment of the resultant azide with the anion of 2-cyanoacetamide provides compound 7.

Compounds 8–10 may be synthesized beginning with their corresponding 3-halobenzylbromides. Conversion of the bromide to an azide can be accomplished using sodium azide in ethanol. The products are then obtained by treating the resultant 3-halobenzyl azides with the anion of 2-cyanoacetamide.

Compound 11 can be obtained beginning with 3-iodobenzylamine. This amine can be converted to its corresponding azide by forming a 2,4,6-triphenylpyrylium derivative and subsequently displacing the pyrylium species using sodium azide. The azide may be treated as above to provide compound 11.

Compound 12 can be prepared from 3,5-difluorobenzamide. In this instance, the benzamide is reduced to 3,5-difluorobenzylamine and the steps used for compound 11 are employed.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A method for detecting and quantifying therapeutic agents in a blood sample, said therapeutic agents comprising compounds of the formula;

$$Z—(CH_2)_p—Ar^1 \qquad (A)$$

wherein:

p is an integer of from 0 to 4;

$Ar^1$ is a moiety selected from the group consisting of $—Ar^2—X—Ar^3$, phenyl, trioxaadamantyl, anthracenyl, anthraquinonyl, naphthyl, phenanthryl, and substituted versions thereof;

$Ar^2$ and $Ar^3$ are each aromatic moieties independently selected from the group consisting of phenyl, naphthyl, and substituted versions thereof;

X is a linking moiety selected from the group consisting of O, S, $SO_2$, CO, CHCN, straight chain alkyl, alkoxy, and alkoxyalkyl; and Z is a nitrogen-containing heterocyclic moiety selected from the group consisting of imidazolyl, 1,2,3-triazolyl, 1,2,4-triazolyl, pyrazinyl, purinyl, pyrimidinyl, 1,2,3-triazolo-{4,5-d}-pyrimidinyl, and substituted versions thereof;

said method comprising the steps:

(a) extracting said therapeutic agents from said blood sample using a solid phase procedure to produce an extract;

(b) subjecting said extract to isocratic reverse phase high performance liquid chromatography using a column having irregular packing to produce a chromatogram; and (c) comparing said chromatogram with a standard to detect and quantify said therapeutic agents.

2. A method in accordance with claim 1 wherein said therapeutic agent is of formula (A), p is an integer of from 0 to 2, $Ar^1$ is $—Ar^2—X—Ar^3$, $Ar^2$ and $Ar^3$ are both substituted phenyl, and Z is a nitrogen-containing heterocyclic moiety selected from the group consisting of imidazolyl, 1,2,3-triazolyl, and substituted versions thereof.

3. A method in accordance with claim 1 wherein said therapeutic agent is of formula (A), p is an integer of from 0 to 2, $Ar^1$ is $—Ar^2—X—Ar^3$, $Ar^2$ and $Ar^3$ are both substituted phenyl, X is a linking moiety selected from the group consisting of O, CO, and CHCN, and Z is a nitrogen-containing heterocyclic moiety selected from the group consisting of imidazolyl, 1,2,3-triazolyl, and substituted versions thereof.

4. A method in accordance with claim 1 wherein said therapeutic agent is of formula (A), p is 1, $Ar^1$ is $—Ar^2—X—Ar^3$, $Ar^2$ and $Ar^3$ are both substituted phenyl, X is CO, and Z is a nitrogen-containing heterocyclic moiety selected from the group consisting of imidazolyl, 1,2,3-triazolyl, and substituted versions thereof.

5. A method in accordance with claim 1 wherein said therapeutic agent is of formula (A), p is 1, $Ar^1$ is $—Ar^2—X—Ar^3$, $Ar^2$ and $Ar^3$ are both substituted phenyl, X is CO, and Z is 5-amino-4-carboxamido-1,2,3-triazolyl.

6. A method in accordance with claim 1 wherein said therapeutic agent is of formula (A), p is 1, $Ar^1$ is $—Ar^2—X—Ar^3$, $Ar^2$ is 2,6-dichlorophenyl, $Ar^3$ is 4-chlorophenyl, X is CO, and Z is 5-amino-4-carboxamido-1,2,3-triazolyl.

7. A method in accordance with claim 1 wherein said solid phase procedure comprises applying said blood sample to a chromatography cartridge packed with a hydrocarbon-bonded silica stationary phase.

8. A method in accordance with claim 1 wherein said solid phase procedure comprises applying said blood sample to a chromatography cartridge packed with a C-18 bonded silica stationary phase.

9. A method in accordance with claim 1 wherein step (b) is carried out using a mobile phase consisting of methanol and a buffered aqueous solution.

10. A method in accordance with claim 9 wherein step (b) is carried out using a mobile phase consisting of methanol and about 0.05–0.5M aqueous ammonium acetate.

11. A method in accordance with claim 9 wherein step (b) is carried out using a mobile phase consisting of about 60–90% methanol and 10–40% 0.1M aqueous ammonium acetate.

12. A method in accordance with claim 1 wherein said irregular packing is hydrocarbon-bonded silica having a size of from about 2 to 25 microns.

13. A method in accordance with claim 12 wherein said irregular packing is hydrocarbon-bonded silica selected from the group consisting of C-8, C-18 and cyclohexyl bonded silica.

14. A method in accordance with claim 12 wherein said irregular packing is C-18 hydrocarbon-bonded silica.

15. A method in accordance with claim 1 wherein said solid phase procedure comprises applying said blood sample to a chromatography cartridge packed with a C-18 bonded silica stationary phase, step (b) is carded out using a mobile phase consisting of about 60–90% methanol and 10–40% 0.1M aqueous ammonium acetate, and said irregular packing is C-18 hydrocarbon-bonded silica having a size of about 10 microns.

* * * * *

UNITED STATES PATENT AND TRADEMARK OFFICE
CERTIFICATE OF CORRECTION

PATENT NO. : 5,405,782
DATED : April 11, 1995
INVENTOR(S) : Elise C. Kohn, Lance A. Liotta, Scott A. Chaffins It is certified that error appears in the above-indentified patent and that said Letters Patent is hereby corrected as shown below:

On the title page, in item [75], add, as the third line, the name and address of third inventor --Scott A. Chaffins, Hilliard, Ohio--.

In column 2, line 23, delete "(CAI)" and substitute therefor --(CAI, carboxyamidotriazole)--.

In column 4, line 27, after "auto", insert a hyphen.

In column 6, line 23, replace "4.5" with --4.6--.

In column 8, line 5, delete "degasseal", and substitute therefor, --degassed--.

In column 14, line 32, delete "carded", and substitute therefor --carried--.

Signed and Sealed this

Twelfth Day of September, 1995

Attest:

BRUCE LEHMAN

*Attesting Officer*    *Commissioner of Patents and Trademarks*